(12) United States Patent
Schade et al.

(10) Patent No.: US 8,850,867 B2
(45) Date of Patent: Oct. 7, 2014

(54) PHOTOACOUSTIC SENSOR AND METHOD FOR THE PRODUCTION AND USE THEREOF

(75) Inventors: Wolfgang Schade, Goslar (DE);
Michael Köhring, Bad Sachsa (DE);
Tobias Schossig, Clausthal-Zellerfeld (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 202 days.

(21) Appl. No.: 13/392,653

(22) PCT Filed: Aug. 24, 2010

(86) PCT No.: PCT/EP2010/062334
§ 371 (c)(1),
(2), (4) Date: Feb. 27, 2012

(87) PCT Pub. No.: WO2011/023695
PCT Pub. Date: Mar. 3, 2011

(65) Prior Publication Data
US 2012/0151995 A1   Jun. 21, 2012

(30) Foreign Application Priority Data
Aug. 28, 2009  (DE) .......................... 10 2009 029 002

(51) Int. Cl.
*G01N 21/17* (2006.01)

(52) U.S. Cl.
CPC .... *G01N 21/1702* (2013.01); *G01N 2021/1704* (2013.01)
USPC ..................................... 73/24.02

(58) Field of Classification Search
None
See application file for complete search history.

(56) References Cited

U.S. PATENT DOCUMENTS

| | | | |
|---|---|---|---|
| 6,082,178 A | 7/2000 | Bernstein et al. | |
| 7,304,732 B1 * | 12/2007 | Polcawich et al. | ............ 356/246 |
| 7,463,364 B2 * | 12/2008 | Yacoubian | ..................... 356/502 |
| 2002/0178787 A1 * | 12/2002 | Matsiev et al. | ............. 73/24.01 |
| 2005/0117155 A1 * | 6/2005 | Kosterev | ........................ 356/432 |
| 2005/0185188 A1 | 8/2005 | McGrew | |
| 2007/0151325 A1 * | 7/2007 | Kauppinen | ................... 73/24.02 |

(Continued)

FOREIGN PATENT DOCUMENTS

| | | |
|---|---|---|
| CH | 686589 A5 | 4/1996 |
| DE | 69610225 T2 | 1/2001 |

(Continued)

OTHER PUBLICATIONS

Stephen et al., Ultra-compact, high efficiency, quartz-enhanced photoacoustic spectroscopy based trace gas sensor platform. Oct. 2006 IEEE.*

(Continued)

*Primary Examiner* — Hezron E Williams
*Assistant Examiner* — Xin Zhong
(74) *Attorney, Agent, or Firm* — Brinks Gilson & Lione

(57) ABSTRACT

A photoacoustic sensor, containing a resonance body, which at least partially delimits a space for receiving molecules to be detected, and a device for detecting an oscillation of the resonance body, including a device for optically detecting the location of at least one partial surface of the resonance body. A method for the photoacoustic detection of molecules in the gas phase and to a method for producing an optically integrated photoacoustic sensor.

20 Claims, 3 Drawing Sheets

(56) References Cited

U.S. PATENT DOCUMENTS

| | | | |
|---|---|---|---|
| 2007/0280605 A1 | 12/2007 | Mendoza | |
| 2008/0138088 A1 | 6/2008 | Welch et al. | |
| 2009/0304331 A1 | 12/2009 | Herman et al. | |
| 2010/0101305 A1* | 4/2010 | Miklos et al. | 73/24.02 |
| 2010/0192669 A1* | 8/2010 | Presura et al. | 73/23.3 |
| 2011/0290002 A1 | 12/2011 | Heidrich et al. | |
| 2012/0321242 A1 | 12/2012 | Schade et al. | |

FOREIGN PATENT DOCUMENTS

| | | | |
|---|---|---|---|
| DE | 102007043951 A1 | 4/2009 | |
| DE | 102008047658 B3 | 1/2010 | |
| DE | 102009014478 A1 | 9/2010 | |
| DE | 102010001197 A1 | 7/2011 | |
| EP | 0871860 B1 | 9/2000 | |
| EP | 0979401 B1 | 1/2002 | |
| JP | 05-172738 | 7/1993 | G01N 21/00 |
| WO | WO 03/104767 A2 | 12/2003 | |
| WO | WO 2006/001842 A2 | 1/2006 | G01J 1/00 |
| WO | WO 2006/092751 A1 | 9/2006 | |
| WO | WO 2010/028865 A1 | 3/2010 | G01N 21/17 |

OTHER PUBLICATIONS

International Search Report with English translation, dated Nov. 11, 2010, International Patent Application No. PCT/EP2010/062334, pp. 1-4, European Patent Office, Rijswijk, The Netherlands.

Chapter 2 International Preliminary Report on Patentability with English translation, International Patent Application No. PCT/EP2010/062334, dated Oct. 31, 2011, pp. 1-33, Munich, Germany.

Bhushan, B. "Springer Handbook of Nanotechnology", dated 2004, pp. 350, Berlin, Germany.

Breguet, J et al. "Photoacoustic, detection of trace gases with an optical microphone" dated May 1, 1995, pp. 29-35, Elsevier Sequoia Inc., Lausanne, Switzerland.

Firebaugh, Samuel L et al. "Miniaturization and integration of photoacoustic detection with a microfabricated chemical reactor system", vol. 10, No. 2, Jun. 2001, pp. 232-237, Journal of Microelectromechanical Systems, IEEE Service Center, Piscataway, New Jersey.

Grober, Robert D et al. "Fundamental limits to force detection using quartz tuning forks", dated Jul. 1, 2000, pp. 2776-2780, Review of Scientific Instruments, AIP, Melville, New York, US.

Katz, O. "Standoff detection of trace amounts of solids by nonlinear Raman spectroscopy using shaped femtosecond pulses", dated May 2, 2008, pp. 171116(1)-171116(3), College Park, Maryland.

Kosterev, A. A. et al. "Quartz-enhanced photoacoustic spectroscopy", dated Nov. 1, 2002, pp. 1902-1904, Optics Letters, Washington, DC, US.

Miklos, Andas et al. "Application of acoustic resonators in photoacoustic trace gas analysis and metrology", dated Jan. 15, 2001, pp. 1-19, Review of Scientific Instruments, American Institute of Physics, Melville, New York, US.

Pohlkotter, Andreas et al. "Resonant tuning fork detector for electromagnet radiation", dated Feb. 1, 2009, pp. 1937-1955, Applied Optics, Washington, DC, US.

Schonenberger, C. "A differential interferometer for force microscopy", dated Oct. 1, 1989, pp. 3131-3134, Review of Scientific Instruments, American Institute of Physics, Melville, New York, US.

* cited by examiner

PHOTOACOUSTIC SENSOR AND METHOD FOR THE PRODUCTION AND USE THEREOF

BACKGROUND

The invention relates to a photoacoustic sensor, comprising a resonance body which at least partly delimits a volume intended to hold molecules to be detected and an apparatus for identifying a vibration of the resonance body.

A. A. Kosterev et al.: Quartz-enhanced photoacoustic spectroscopy, Optics Letters, Vol. 27, No. 21 (2002) 1902 has disclosed a device of the type mentioned at the outset. This known detection method discloses the use of a fork-shaped quartz crystal as a highly sensitive microphone, by means of which pressure variations in a gas phase can be detected. According to the known method, the pressure variations are generated by means of a laser diode, which selectively excites the molecules in the gas phase by means of spectrally narrow-band radiation. The sensitivity of the photoacoustic measurements can be increased due to the high Q-factor of the fork-shaped quartz crystal used for the detection.

However, the method known from the prior art is disadvantageous in that the material selection for producing the fork-shaped element is restricted to piezoelectric materials. Hence, the signal processing requires the measurement of a signal voltage lying between a few picovolts and a few nanovolts. Measuring such small voltages is susceptible to electric disturbance signals. Furthermore, the known photoacoustic gas sensor cannot be used in explosive gas atmospheres because the piezoelectric sensor can cause an explosion by voltage sparkovers. Finally, the known measurement method cannot be used in hot gas atmospheres either because the piezoelectric materials used fail if the temperature is too high.

Proceeding from this prior art, the invention is therefore based on the object of specifying a method for gas analysis, which can be applied universally, even at high temperatures and in potentially explosive regions. Furthermore, the method should have increased reliability with respect to electric disturbance signals.

SUMMARY

According to the invention, it is proposed to excite the molecules situated in the gas atmosphere selectively by narrow-band laser radiation from a continuous wave laser or by appropriately shaped laser pulses with a duration of less than 200 fs. According to the invention, in order to detect the excitation that took place, a photoacoustic sensor is proposed, which comprises a resonance body which at least partly delimits a volume intended to hold molecules to be detected. This allows a pressure variation arising during the deexcitation of the optically excited molecules to be detected as a photoacoustic signal.

The intensity of this photoacoustic signal is proportional to the concentration of the molecules to be detected. Different molecules can be excited by different wavelengths of the laser light used for the excitation or by differently shaped pulses of a short-pulse laser with pulse lengths of less than 200 fs. This affords the possibility of testing the composition of a gas mixture and/or the presence or absence of a molecule to be detected in the gas mixture.

According to the present invention, the vibration of the resonance body is identified by means of an apparatus for optically capturing the location of at least one subarea of the resonance body. In another embodiment of the invention, the location of a subarea of the resonance body can be determined by means of an interference signal. This method is distinguished by a very high accuracy because the location can be used down to a fraction of the wavelength of the light used for the measurement. As a result of the long coherence length, it is advantageously possible to use the light of a laser for optically capturing the location of at least one subarea of the resonance body.

In some embodiments of the invention, the resonance body can have at least two prongs, arranged approximately in parallel, which are respectively fixed to a connection element with a foot point and project freely at the end thereof opposite to the foot point. This results in the optical impression of a fork or a rake. In some embodiments, such a resonance body can simplify the spectroscopic detection of gaseous molecules if the at least two prongs, arranged approximately in parallel, at least partly delimit the measurement volume in which the molecules to be detected are situated. This enables a direct influence of the pressure variation arising when the molecules are excited on the at least two prongs arranged approximately in parallel. Furthermore, this geometry enables an efficient suppression of coupled-in air sound if the length of and/or the distance between the at least two prongs arranged approximately in parallel is selected to be smaller than the wavelength of the sound acting on the device.

In some embodiments of the invention, the sensor comprises at least one beam displacer with at least one input and at least two outputs, designed to split an input laser beam into a plurality of output laser beams, the latter being provided for being reflected at different subareas of the resonance body. This results in a particularly low-disturbance and reliable evaluation of the photoacoustically induced vibration of the resonance body. As a result of the reflection at two subareas vibrating with different amplitudes, the two laser beams experience a phase shift that can be detected very easily as a measurable change in intensity after the two beams are brought together and subsequently separated according to polarization direction.

In some embodiments of the invention, the laser light used to excite the molecules to be detected can be coupled-in as a free beam. To this end, some embodiments of the invention can make use of optical prongs such as slits, stops or lenses. In other embodiments of the invention, the light used to excite the molecules to be detected can be supplied by means of a waveguide. This enables a particularly space-saving design, which is not susceptible to faults, of the sensor proposed according to the invention.

In some embodiments, the sensor proposed according to the invention can be integrated in a single substrate in monolithic form. The substrate can comprise an optically transparent material. In some embodiments of the invention, the substrate can comprise quartz glass or sapphire or magnesium oxide or langasite. In other embodiments of the invention, the substrate can comprise a polymer. In one embodiment of the invention, the substrate can comprise polymethyl methacrylate.

In some embodiments of the invention, the substrate can be processed with the aid of a pulsed laser such that both waveguides and mechanically movable microstructures are produced in an optically transparent substrate. Here, the interaction of laser pulses, e.g. laser pulses with a duration of less than 250 fs, can induce a change in the refractive index. The change in the refractive index can be introduced into the material in a punctiform and three-dimensional fashion by focusing the laser beam used for the material processing. By overlapping the respective points it is possible to introduce a structure with a longitudinal extent, e.g. a waveguide, into the material. In some embodiments of the invention, the laser pulses used for processing the material can be modulated in terms of their amplitude and/or phase.

In a further embodiment of the invention, provision can be made for areal regions in the substrate, which are exposed by the laser beam used to process the substrate, to be etched by means of an acid. By way of example, this can be brought about by means of HF.

BRIEF DESCRIPTION OF THE DRAWINGS

In the following text, the invention is intended to be explained in more detail on the basis of exemplary embodiments and figures, without this restricting the general inventive concept. In detail.

DESCRIPTION OF PREFERRED EMBODIMENTS

Figure 1:
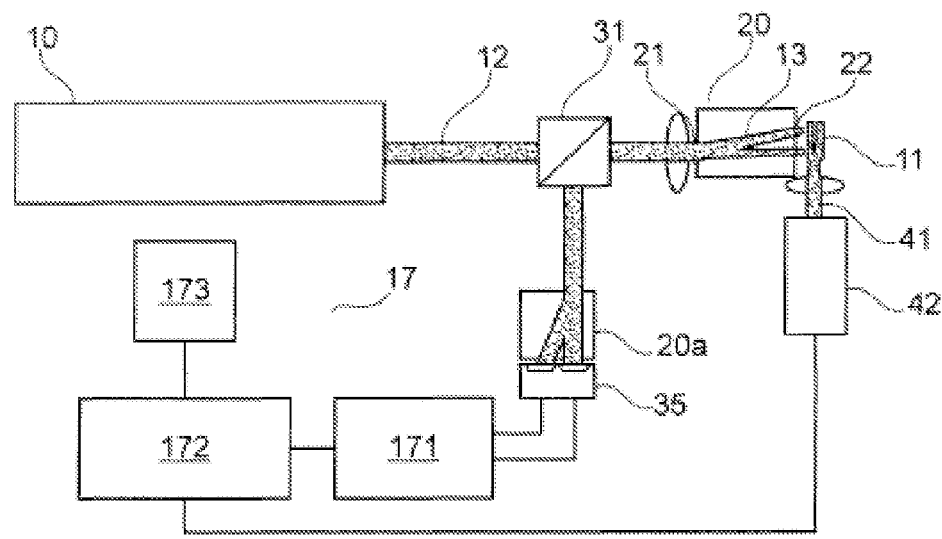
FIG. 1 shows the measurement principle, proposed according to the invention, for optical readout of the photoacoustic sensor according to one embodiment of the invention.

FIG. 1 shows an embodiment of the measurement principle, proposed according to the invention, for optical readout of the photoacoustic sensor. The gas comprising the molecules to be detected surrounds a resonance body 11. In some embodiments of the invention, the resonance body 11 can have at least two prongs, arranged approximately in parallel, which are respectively fixed to a connection element with a foot point and project freely at the end thereof opposite to the foot point. In this case, the volume 18 intended to hold the gas with the molecules to be detected is situated between the two prongs arranged approximately in parallel.

The molecules to be detected are excited by means of a light beam 41. The light beam 41 can be provided by means of a laser 42. By way of example, the laser 42 can be a diode laser or a femtosecond laser. Accordingly, the light beam 41 comprises laser radiation with a narrow spectral band, which can selectively excite at least one electronic transition, a rotational transition or a vibrational transition in the molecules to be detected. To the extent that the laser 42 is a femtosecond laser, the light beam 41 comprises laser pulses with a duration of less than 200 fs, less than 100 fs, less than 50 fs or less than 20 fs. In this case, modulating the amplitude and/or the phase of the laser pulses can selectively excite at least one rotational and/or vibrational excitation in the molecules to be detected.

The optical excitation of the molecules to be detected leads to the transfer of translation energy onto the molecules, which causes a pressure variation. The pressure variation in turn excites a vibration of the resonance body 11.

The vibration of the resonance body 11 is captured by means of an optical apparatus. The apparatus for capturing the vibration comprises a laser 10, e.g. a He—Ne laser or a laser diode. The laser 10 provides a laser beam 12 that is provided to capture the vibration of the resonance body 11 by measuring the location of at least one areal region 116 of the resonance body 11. To this end, an interferometer is available in the embodiment illustrated in FIG. 1.

The interferometer comprises a beamsplitter 31. The beamsplitter is an optical element that splits an incident light beam 12 into two light beams. In some embodiments of the invention, the beamsplitter can comprise a cube that is composed of two triangular glass prisms. A first part of the light is reflected at and a second part of the light is transmitted on the interface running diagonally through the cube. In other embodiments of the invention, the beamsplitter can comprise a semi-transparent mirror. The semi-transparent mirror can comprise a glass plate, which is provided with a vapor-deposited coating made of a metal or an alloy. The metal or the alloy can comprise aluminum. In some embodiments of the invention, the first part of the light and the second part of the light can each comprise approximately 50% of the irradiated light 12.

The light leaving the beamsplitter in a straight direction reaches a beam displacer 20. The beam displacer 20 has at least one input 21 and at least two outputs 22. The beam displacer 20 divides the entering light beam 12 into at least two emerging light beams 13. In some embodiments of the invention, the beam displacer can comprise a Wollaston prism, a Rochon prism, a Glan-Thomson prism or a Nicol prism. The aforementioned prisms comprise a birefringent material. The refractive index of such a birefringent material depends on the polarization of the entering light 12. As a result, light with a first polarization direction and light with a second polarization direction respectively take a different path through the material of the prism. As a result, a first light beam 13 with a first polarization and a second light beam 13 with a second polarization are available at the output of the beam displacer.

One of the light beams 13 at the output of the beam displacer 20 can be used as a reference beam. The other light beam 13 at the output of the beam displacer 20 can be used as a detection beam. The two beams are reflected at different subareas of the resonance body 11. As a result of the vibration of the resonance body 11, the detection beam experiences a phase shift relative to the reference beam. Both reflected light beams are once again coupled into the beam displacer 20 through the outputs 22. The light beams 13 reflected at the resonance body 11 are brought together in the beam displacer 20 and leave the beam displacer via the input 21 thereof in the direction of the beamsplitter 31.

In the beamsplitter 31, the light reflected at the resonance body 11 is reflected and routed to a second beamsplitter 20a. In the beamsplitter 20a, the light reflected at the resonance body 11 is once again split into the reference beam and the detection beam as a result of the polarization dependence of the refractive index in the interior of the beamsplitter 20a.

A photodiode 35 enabling a spatially dependent detection of the incident light is available at the output of the beamsplitter 20a. In some embodiments of the invention, the photodiode 35 can be a quadrant photodiode. In other embodiments of the invention, the photodiode 35 can be formed by two photodiodes, of which one detects the detection beam and one detects the reference beam.

The electric signal from the photodiode 35 is captured by means of electronics 171. Here, the electronics 171 can comprise a voltage supply, by means of which it is possible to apply a bias voltage to the photodiode 35. Furthermore, the electronics 171 can comprise a preamplifier and/or a discriminator, by means of which the signals from the photodiode 35 are processed further. Moreover, the electronics 171 can comprise an analog-to-digital converter in order to process further the analog output signals from the photodiode 35 by means of digital electronics. In some embodiments of the invention, the electronics 171 can comprise an arithmetic unit that forms the quotient of the difference between the two signals and the sum of the two signals as per the following formula:

$$f = \frac{a+b}{a-b}.$$

In some embodiments of the invention, the electronics 171 can comprise an arithmetic unit that forms the difference between the two signals as per the following formula:

$f=a-b.$

In order to increase the detection sensitivity and to suppress background signals, the laser 42 can, in some embodiments of the invention, be modulated by the resonant frequency of the resonance body 11 or by a frequency that constitutes an integer multiple of the resonant frequency. This enables the measurement signal provided at the output of the electronics 171 to be evaluated by means of a lock-in amplifier 172. The data from the lock-in amplifier 172 can be stored and/or visualized by means of a digital measurement system 173. Here, the measurement system 173 may comprise a personal computer.

Figure 2:
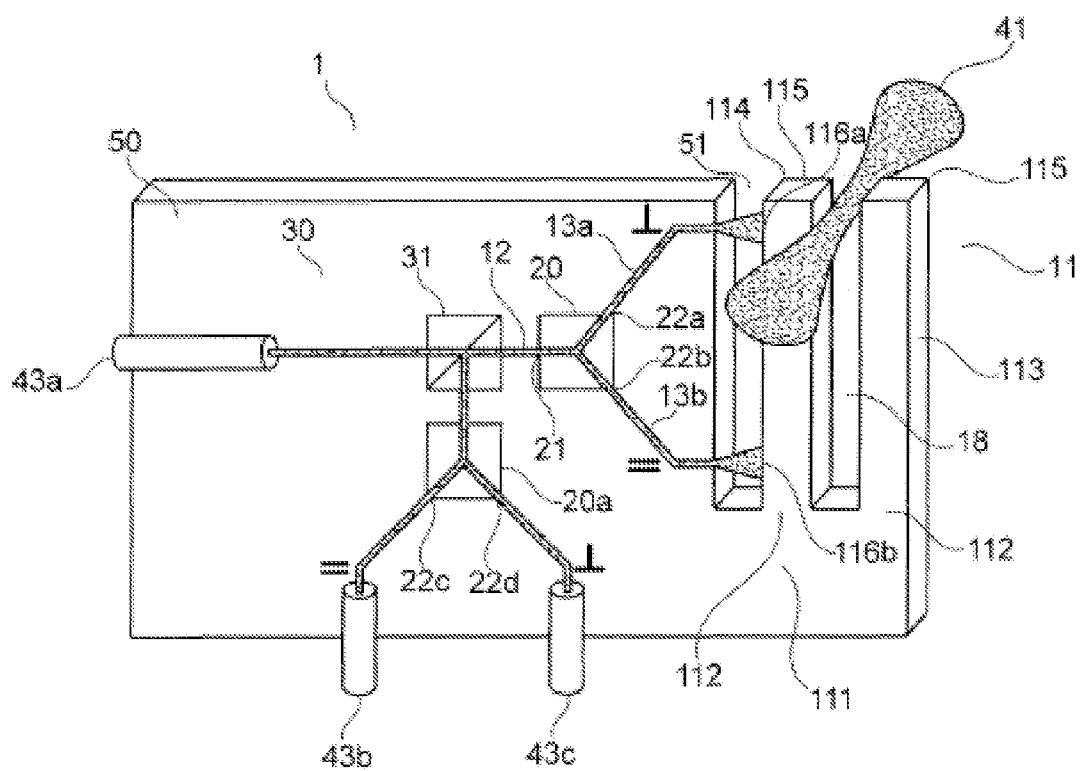
FIG. 2 illustrates a first embodiment of a photoacoustic sensor, as proposed according to the invention.

FIG. 2 shows an exemplary embodiment of a photoacoustic sensor 1, as proposed according to the invention. The photoacoustic sensor 1 comprises the resonance body 11 and parts of the interferometer 30 in an integrated design. According to the embodiment illustrated in FIG. 2, the resonance body 11 and the interferometer 30 are integrated in monolithic form in a single substrate 50.

Two recesses 18 and 51 have been introduced into the substrate 50; these free up two elongate prongs 114 and 113. The recesses can be produced by means of micromechanical processing methods. The recesses 18 and 51 can be produced by means of etching, sawing, milling or another processing method, known per se, such that this results in the impression of a slit in the substrate 50. The recesses can have a width of between approximately 10 µm and approximately 500 µm. The recesses 51 and 18 encompass the substrate 50 in its entire thickness.

The prongs 114 and 113 are respectively connected to a connection element 111 at a foot point 112. The end 115 opposite to the foot point 112 projects freely. As a result of this, the elongate prongs 114 and 113 can vibrate at a resonant frequency that depends on the geometric dimensions of the prongs 114 and 113, and on Young's modulus of the material of the substrate 50. In some embodiments, the prongs 113 and 114 can have a length of between approximately 100 µm and approximately 10 000 µm, and a width of between approximately 50 µm and approximately 1000 µm.

Between the elongate prongs 113 and 114 there is a volume 18 provided for holding the molecules to be detected. A light beam 41 is available to excite the molecules, as described in conjunction with FIG. 1. Since the volume 18 is formed by a continuous recess which encompasses the substrate 50 in its entire thickness, the light beam 41 can be supplied as a free beam in the embodiment as per FIG. 2. To this end, the light beam 41 is irradiated in a plane that is approximately perpendicular to the plane of the measurement beam 13a and the reference beam 13b. This prevents the light beam 41 from being directly incident on the resonance body 11 or the elongate element 114 and the measurement signal from being falsified by the acting photon pressure.

An interferometer 30 is available for optically capturing the vibration of the elongate element 114. Like the resonance body 11, the interferometer 30 is also integrated in the substrate 50 in monolithic form. The interferometer 30 comprises a beamsplitter 31, as explained in conjunction with FIG. 1. Light from a laser is routed to the beamsplitter 31 by means of an optical waveguide. The optical waveguide starts at a plug-in connection 43a, which is provided for holding a glass fiber in a manner known per se. Further optical waveguides open at the outputs of the beamsplitter 31; these connect the beamsplitter 31 to respective beam displacers 20 and 20a.

The beam displacer 20 has one input 21 and two outputs 22a and 22b. The beam displacer 20 can comprise a birefringent material, as explained in conjunction with FIG. 1. A measurement beam 13a that is incident on a subarea 116a of the elongate element 114 is available at the output 22a of the beam displacer 20. A reference beam 13b that is incident on a second subarea 116b of the elongate element 114 is available at the output 22b of the beam displacer 20. Since the subarea 116b lies closer to the foot point 112 of the elongate element 114, the vibration amplitude of the areal element 116b when the element 114 vibrates is less than the amplitude of the areal element 116a. As a result of this difference, the reflected light beams 13a and 13b experience a phase shift when the elongate element 114 vibrates and this can be measured by interferometry.

The light reflected at the areas 116a and 116b is introduced into the beam displacer 20 via the outputs 22a and 22b, which now act as inputs of the beam displacer 20, and is decoupled from the beam displacer 20 via the input 21, which now acts as output.

The light reflected at the areas 116a is subsequently reflected at the beamsplitter 31 and enters the second beam displacer 20a. The beam displacer 20a has two outputs 22c and 22d. Light from the reference beam 13b reaches the output 22c of the beam displacer 20a as a result of its polarization direction. Light from the measurement beam 13a reaches the output 22d of the beam displacer 20a as a result of its polarization direction, which differs from that of the beam 13b. The signals from the outputs 22c and 22d reach associated plug-in connectors 43b and 43c via appropriate optical waveguides, which are formed in the substrate 50. The plug-in connectors 43b and 43c are also provided for holding a glass fiber in a manner known per se. The light can be routed to at least one photodiode and to evaluation electronics via this glass fiber, as explained in conjunction with FIG. 1.

The optical elements of the interferometer 30, such as the beamsplitter 31 and/or the beam displacer 20 and/or the beam displacer 20a and/or the optical waveguides that interconnect the aforementioned elements or connect these to the plug-in connectors 43a, 43b and 43c can, in some embodiments of the invention, be introduced into the substrate 50 with the aid of laser material processing.

In one embodiment of the invention, the laser material processing can comprise the irradiation of laser pulses that have a duration of less than 250 fs, less than 100 fs, less than 50 fs or less than 20 fs. It is possible to induce a change in the refractive index as a result of the interaction of the laser pulses with optically transparent materials such as e.g. quartz glass, magnesium oxide, langasite, sapphire, polymethyl methacrylate or other polymers. As a result, the substrate 50 has first regions with a first refractive index and second regions with a second refractive index. There is a jump in the refractive index, at which there can be total-internal reflection of light, at the transition regions between the irradiated and the non-irradiated regions. This allows the irradiated region to be used as an optical element, for example as a waveguide. By selecting a two-dimensional spatial coordinate and a position of the focus of the laser beam, it is possible to induce the change in refractive index in three dimensions in the substrate 50. The surface roughness can be optimized by modulating the amplitude and/or phase of the laser pulses used for the material processing.

Furthermore, exposed material can be attacked by an etching means which attacks unexposed material to a lesser extent. By way of example, the etching step can be carried out as a wet chemical or dry chemical etching step. This also makes it possible to produce the mechanical structures, for example the plug-in connectors 43 and/or the resonator 11, by exposing and etching the substrate 50. The recesses 51 and 18 can also be produced in this fashion.

Figure 3:
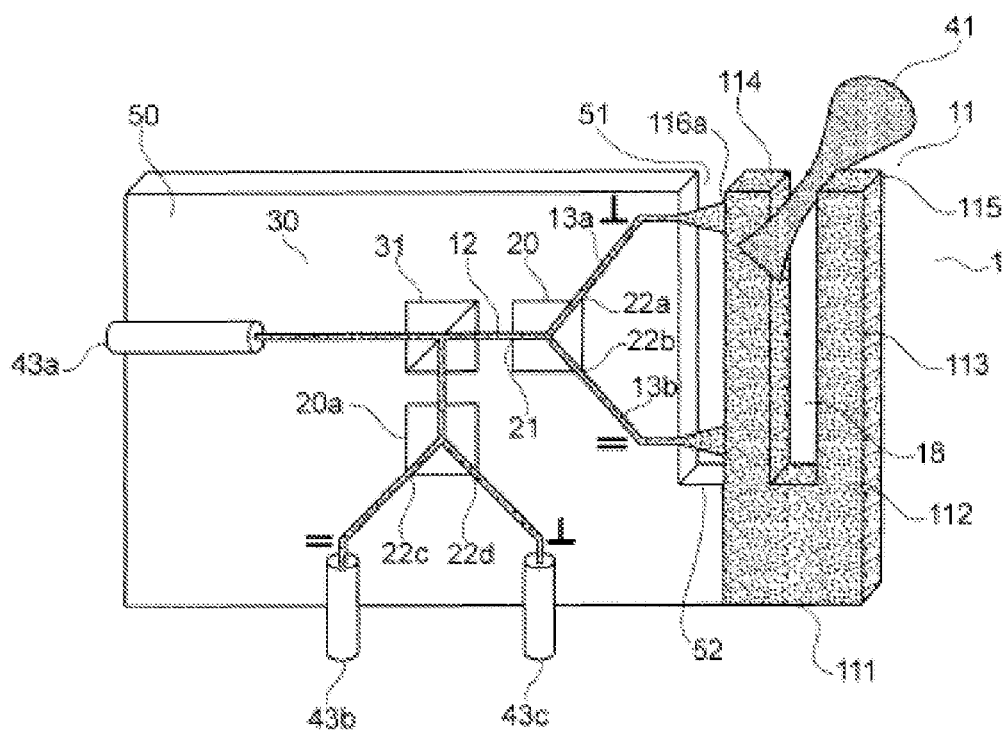
FIG. 3 illustrates a second embodiment of a photoacoustic sensor according to the present invention.

FIG. 3 shows a further embodiment of the present invention. The embodiment as per FIG. 3 also comprises a resonance body 11, which surrounds a volume 18 in which the molecules to be detected can be introduced. Provision is once again made for a light beam 41 to excite the molecules to be detected, as described in conjunction with FIGS. 1 and 2.

An apparatus 17 is available for optically identifying the vibration of the resonance body 11. The apparatus 17 comprises an interferometer 30, as described in conjunction with FIG. 2.

Deviating from FIG. 2, the photoacoustic sensor as per FIG. 3 is not completely integrated in monolithic form. According to FIG. 3, the resonator 11 is made of a first material and the apparatus 17 for optically capturing the vibration of the resonator 11 is made of a substrate 50 made of a second material. This makes it possible to use respectively optimized materials, which achieve the respective objects to the best possible extent, for both the resonator 11 and also for the apparatus 17. By way of example, a material can be selected for the apparatus 17 into which the optical components can be introduced in a particularly simple fashion by means of laser material processing. Alongside this, a material whose Young's modulus has been optimized to the extent that the resonant frequency of the resonator 11 is in a desired range for predeterminable geometric dimensions can be selected for the resonator 11. Furthermore, the material of the resonator 11 can be selected such that the resonator 11 has good reflection properties, at least on those subareas 116 on which the laser beams 13 are reflected.

The joint between the resonator 11 and the apparatus 17 can for example be brought about by adhesive bonding, being screwed together, a clamping point or welding, or by further contacting methods not explicitly mentioned. The recess 51 is obtained by shaping a step 52 in the substrate 50 when forming the joint between the apparatus 17 and the resonator 11.

In a development of the embodiment as per FIG. 3, the apparatus 17 can be present twice. This makes it possible to use the first apparatus 17 to monitor the vibration of the element 114. The second apparatus 17, which is attached on the resonator 11 symmetrically with respect to the volume 18, can be used to capture the vibration of the element 113. This makes it possible to distinguish between in-phase vibrations of the prongs 113 and 114 and opposite-phase vibrations of the prongs 113 and 114 in order thereby to identify a background signal that can arise as a result of surrounding sound acting on the resonator 11.

Figure 4:
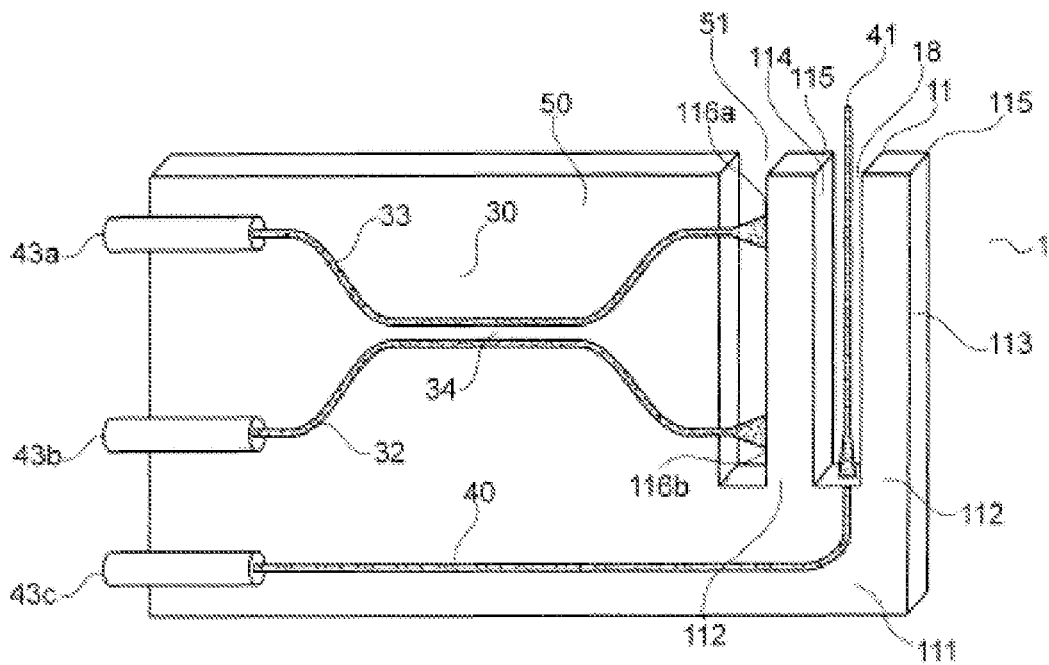
FIG. 4 shows a third embodiment of the photoacoustic sensor according to the present invention.

FIG. 4 shows a further embodiment of the present invention. The photoacoustic sensor as per FIG. 4 is also integrated in monolithic form in a single substrate 50. The photoacoustic sensor as per FIG. 4 in turn comprises two elongate prongs 113 and 114, which partly delimit a volume 18 and a recess 51. The prongs 113 and 114 are respectively fixed to a connection element 111 with a foot point 112. The end 115 opposite to the foot point 112 projects freely and thereby enables a bending vibration of the prongs 114 and 113. Capturing the vibration of the element 114 is brought about by means of a Mach-Zehnder interferometer 30. The Mach-Zehnder interferometer 30 comprises two optical waveguides 32 and 33, which are routed in parallel in a subsection 34. This results in evanescent coupling between the signals carried in the two waveguides 32 and 33.

During the operation of the photoacoustic sensor 1, a coherent light signal, e.g. from a laser, is coupled in via the plug-in connection 43a, which is provided for holding an optical fiber. The light propagates through the waveguide 33 and reaches the subarea 116a of the element 114 as detection beam.

As a result of the evanescent coupling between the waveguides 32 and 33 in the subsection 34, part of the coupled-in light reaches the subarea 116b of the element 114 as reference beam. As a result of the vibration of the element 114, the light signals reflected at the subareas 116a and 116b experience a phase shift. The reflected light signals once again run through the respective waveguides 32 and 33. There is interference between the phase-shifted reflected signals in the region of the subsection 34. The interference pattern can then be captured by means of a photodiode connected to the plug-in connector 43b by means of an optical fiber. The signal processing of the electric signal provided by the photodiode is then brought about as described in conjunction with FIG. 1.

A light beam 41 is once again available for the photoacoustic excitation of the molecules to be detected that are situated in the volume 18. The light beam 41 is once again coupled-in in a plane that runs perpendicular to the plane of the optical waveguides 32 and 33. Contrary to the illustration in FIGS. 2 and 3, the light beam 41 in the embodiment as per FIG. 4 is not routed into the volume 18 as a free beam, but rather it is routed there by means of a waveguide 40. The waveguide 40 likewise ends in a plug-in connector 43c, which is provided for holding an optical fiber. The light beam 41 can be a narrow-band or broad-band beam, be continuous or pulsed, as already explained in conjunction with FIGS. 1 and 2.

Independently of whether the light beam 41 is routed into the volume 18 by means of an optical fiber 40 or as a free beam, care should be taken that this light beam does not impinge on the prongs 114 and 113. This can lead to a disturbance signal as a result of the photon pressure of the light beam 41, which leads to a worsening detection limit or worsening sensitivity of the photoacoustic sensor.

In order to produce the photoacoustic sensor 1 as per FIG. 4, the optical waveguides 32, 33 and 34 can be introduced into the substrate 50 by means of laser material processing, as described in conjunction with FIG. 2. In other embodiments of the invention, optical waveguides, e.g. glass fibers, can also be embedded into a substrate 50.

Figure 5:
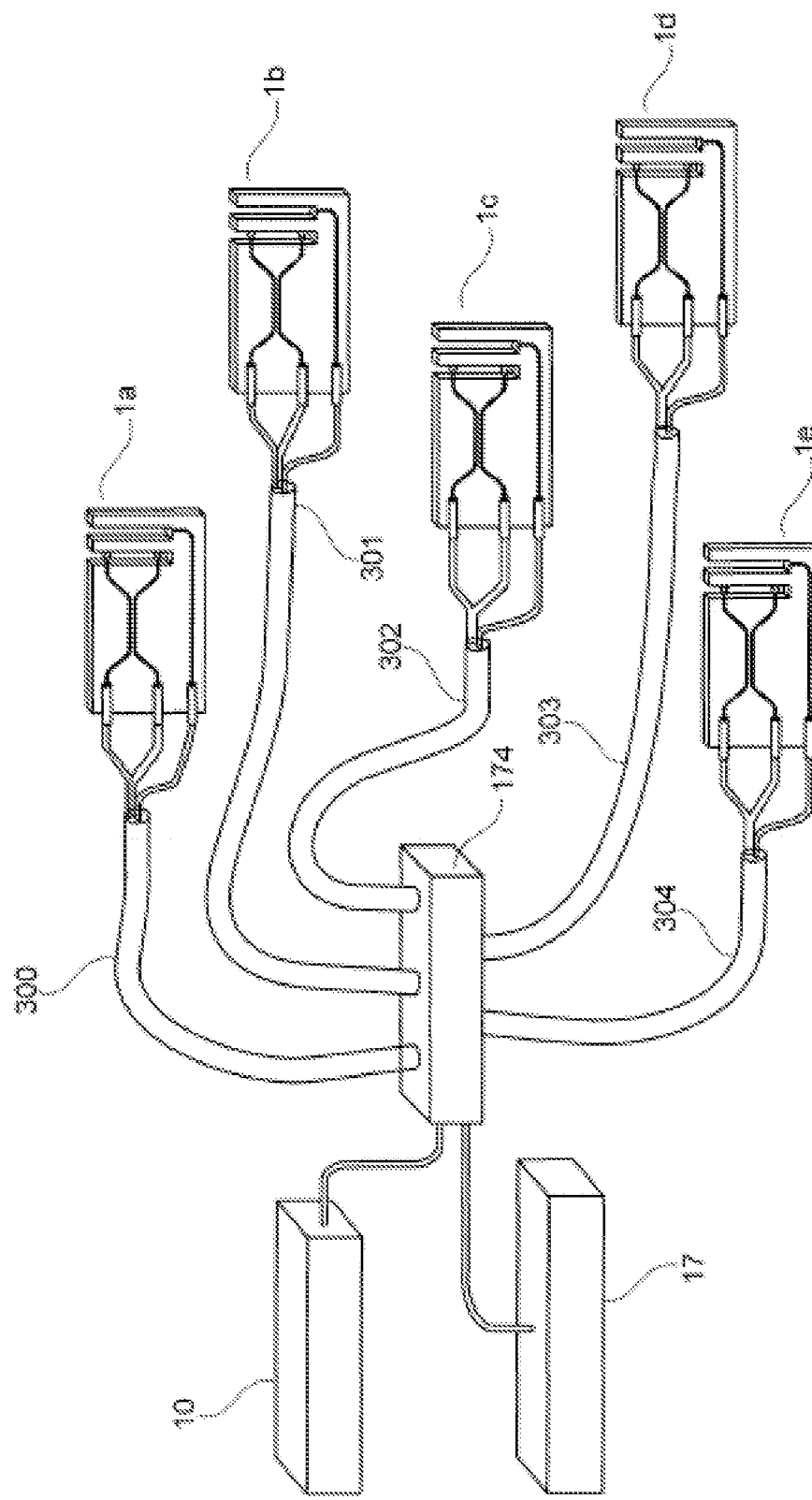
FIG. 5 shows an embodiment of a sensor system with a plurality of sensors.

FIG. 5 shows a sensor system with a plurality of sensors 1a, 1b, 1c, 1d and 1e as illustrated in FIG. 4. The plurality of sensors 1 are respectively connected to a multiplexer 174 by means of a fiber bundle 300, 301, 302, 303 and 304 of optical waveguides. The multiplexer 174 sequentially connects the respective sensors 1a, 1b, 1c, 1d and 1e to a laser light source 10 and an apparatus 17 for evaluating the recorded output signals of the interferometer 30. This enables a plurality of photoacoustic sensors 1, which are respectively connected to the evaluation apparatus 17 in a cycle, to be kept available for a plurality of different molecules to be detected in one embodiment of the invention. This enables various different molecules to be detected in the gas phase to be examined with only short switching times of the multiplexer 174. In another embodiment of the invention, a predeterminable molecule to be detected can be detected at different locations using only one light source and/or one evaluation apparatus.

In order to ensure that individual photoacoustic sensors can be distinguished amongst the plurality of photoacoustic sensors, the photoacoustic sensors can have individual resonant frequencies in some embodiments of the invention.

It is self-evident that the illustrated exemplary embodiments can be combined in order thus to obtain further, different embodiments of the invention. The description above should therefore not be construed as restrictive, but rather be considered explanatory. The claims below should be understood such that a mentioned feature is present in at least one embodiment of the invention. This does not preclude the presence of further features. To the extent that the claims define "first" and "second" features, this designation serves to distinguish between two identical features, without setting an order.

The invention claimed is:

1. A photoacoustic sensor, comprising
a resonance body delimiting at least partly a volume being intended to hold molecules to be detected, and
an apparatus for determining a vibration of the resonance body, comprising means for optically capturing a location of at least one subarea of the resonance body with at least two laser beams, wherein the resonance body is positioned for irradiation of the volume by a light in a plane that is approximately perpendicular to a plane of the at least two laser beams, wherein
the resonance body and the apparatus for determining a vibration being arranged on a substrate, and wherein
the resonance body is formed by at least one slit in the substrate and
wherein the substrate comprises at least one of sapphire, langasite, magnesium oxide, and polymethyl methacrylate.

2. The sensor according to claim 1, the resonance body comprises at least two elongated prongs having a first end and an opposing second end, wherein the elongated prongs are arranged approximately in parallel to each other and are respectively fixed with their first ends to a connection element, wherein the second ends project freely and the volume for holding molecules to be detected is located at least partly between the two prongs.

3. The sensor according to claim 1, furthermore comprising at least one beam splitter having at least one input and at least two outputs, which is adapted to split an input laser beam into a plurality of output laser beams including the at least two laser beams, said output laser beams being intended for being reflected at different subareas of the resonance body.

4. The sensor according to claim 1, wherein the apparatus for determining a vibration comprises an interferometer.

5. The sensor according to claim 4, wherein the interferometer comprises a beam splitter.

6. The sensor according to claim 4, wherein the interferometer comprises at least two waveguides, which are routed in parallel in a subsection, thereby allowing crosstalk between the respective signals guided on the waveguides.

7. The sensor according to claim 4, comprising further at least one photodiode being adapted to detect the output signal of the interferometer.

8. The sensor according to claim 1, comprising further at least one waveguide being adapted to guide light for generating a photoacoustic signal into the volume being intended to hold the molecules to be detected.

9. The sensor according to claim 1, wherein the substrate is a single substrate, the sensor being monolithically integrated on the single substrate.

10. The sensor according to claim 9, wherein the substrate comprises quartz glass.

11. A sensor system comprising a plurality of sensors according to claim 1, wherein each sensor has a resonant frequency that differs from the resonant frequency of the other sensors.

12. A photoacoustic sensor, comprising
a resonance body delimiting at least partly a volume being intended to hold molecules to be detected, and
an apparatus for determining a vibration of the resonance body, comprising means for optically capturing the location of at least one subarea of the resonance body with at least two laser beams, wherein
the resonance body and the apparatus for determining a vibration being arranged on a substrate such that the resonance body is positioned for irradiation of the volume by a light that is in a plane approximately perpendicular to a plane of the at least two laser beams, and wherein
the resonance body is formed by at least one slit in the substrate and
the resonance body comprises at least two elongated prongs having a first end and an opposing second end, wherein the at least one elongated prongs are arranged approximately in parallel to each other and are respectively fixed with their first ends to a connection element, wherein the second ends project freely and the volume for holding molecules to be detected is located at least partly between the two prongs.

13. The sensor according to claim 12, wherein the apparatus for determining the vibration comprises at least two waveguides, which are routed in parallel in a subsection, thereby allowing crosstalk between respective signals guided on the waveguides.

14. The sensor according to claim 12, wherein the apparatus for determining a vibration comprises an interferometer.

15. The sensor according to claim 12, comprising further at least one waveguide being adapted to guide light for generating a photoacoustic signal into the volume being intended to hold the molecules to be detected.

16. A method for spectroscopic detection of molecules, said method comprising the following steps:
introducing the molecules to be detected into a volume that is at least partly delimited by a micromechanical resonance body,
supplying light for generating a photoacoustic signal into said volume,
allowing the molecules to be detected to interact with the resonance body, thereby causing a vibration of the resonance body,
detecting said vibration of the resonance body by optically detecting the location of at least two subareas of the resonance body by means of at least two laser beams,
wherein the light for generating a photoacoustic signal is irradiated in a plane perpendicular to a plane of the at least two laser beams.

17. The method according to claim 16, wherein detecting the vibration of the resonance body involves at least the following steps:
routing an input laser beam to a beam splitter having at least one input and at least two outputs;
splitting the input laser beam into a plurality of output laser beams comprising the at least two laser beams; and
reflecting each laser beam out of the plurality of output laser beams at different subareas of the resonance body.

18. The method according to claim 16, wherein a first laser beam reflected at a subarea of the resonance body is brought into interference with a second laser beam, the first laser beam and the second laser beam included in the at least two laser beams.

19. The method according to claim 16, wherein the wavelength and/or the pulse shape of the light for generating a photoacoustic signal is modified.

20. The method according to claim 16, wherein the light for generating a photoacoustic signal is supplied by means of an optical waveguide.

* * * * *